United States Patent [19]

Gang et al.

[11] Patent Number: 5,235,975
[45] Date of Patent: Aug. 17, 1993

[54] CARDIAC PACEMAKER COMPRESSION HARNESS

[75] Inventors: Eli S. Gang, Los Angeles; H. Stephen Cookston, Malibu, both of Calif.

[73] Assignee: Pressure Products Medical Supplies, Inc., Rancho Palos Verdes, Calif.

[21] Appl. No.: 819,907

[22] Filed: Jan. 13, 1992

[51] Int. Cl.⁵ .............................................. A61F 7/00
[52] U.S. Cl. ...................................... 607/108; 602/19; 128/875
[58] Field of Search ............... 128/399, 400, 402, 403, 128/379, 380, 875, 876, DIG. 15, DIG. 19; 62/530, 259.3; 602/19

[56] References Cited

U.S. PATENT DOCUMENTS

| | | | |
|---|---|---|---|
| 2,252,357 | 8/1941 | Shaw | 128/875 |
| 3,554,190 | 1/1971 | Kaplan | 602/19 |
| 4,198,964 | 4/1980 | Honneffer | 602/19 |
| 4,586,506 | 5/1986 | Nangle | 128/403 |
| 4,589,406 | 5/1986 | Floret | 602/19 |
| 4,598,701 | 7/1986 | Schaefer | 602/19 |
| 4,805,620 | 2/1989 | Meistrell | 128/403 |
| 4,947,870 | 8/1940 | Larcher | 602/19 |
| 4,976,262 | 12/1940 | Palmacci | 128/402 |
| 5,016,629 | 5/1991 | Kanare | 128/402 |
| 5,020,536 | 6/1991 | Keen | 128/402 |
| 5,020,711 | 6/1991 | Kelley | 128/402 |
| 5,072,598 | 12/1991 | Dibrell | 128/403 |
| 5,072,875 | 12/1991 | Zacoi | 128/380 |

Primary Examiner—Mark S. Graham
Attorney, Agent, or Firm—Daniel L. Dawes

[57] ABSTRACT

A therapeutic device for providing cold treatments to cardiac pacemaker implantation patients is comprised of a bilobed chest pad having an elastic chest strap connected thereto. The chest strap is fixed at one end to the lower lobe of the chest pad and is wrapped around the torso of the patient under tension and temporarily is coupled to the opposing portion of the lower lobe of the chest pad. The cold compress, which is placed behind the chest pad over the incision site, is thereby firmly kept in contact with the incision site. A shoulder strap is slidingly coupled at one end to the chest strap and is positioned on the back of the patient and wrapped under tension behind the back and over the shoulder of the patient, which shoulder is adjacent to the incision site. The end of the shoulder strap is then temporarily coupled to the upper lobe of the chest pad. The shoulder strap, substantially adds to the compression on the cold compact and retains the chest pad and shoulder strap in place notwithstanding normal activity of the patient. As a result, the patient is able to move about and engage in normal activities very soon after cardiac implantation and yet continue to receive the benefits of thermal therapy to minimize the trauma normally associated with a subcutaneous cardiac pacemaker implantation.

5 Claims, 1 Drawing Sheet

CARDIAC PACEMAKER COMPRESSION HARNESS

BACKGROUND OF THE INVENTION

1. Field of the Invention

The invention relates to a medical apparatus, and more specifically to treatment apparatus used in connection with pacemaker implantations.

2. Description of the Prior Art

Subcutaneous pacemaker implants are common throughout the world and many thousands occur each year in the United States alone. The procedure has been simplified such that in many instances the operation is carried out in the physician's office. Under current practice, after the pacemaker is implanted subcutaneously through an incision against the chest wall, the incision is then sutured and a gauze bandage is taped over the implant site to protect and keep the incision site sterile during the healing process. Typically, any swelling or hematoma, which is caused by the trauma of implantation, is left untreated and healing is left to normal body processes. However, in some patients, this trauma is pronounced and very uncomfortable. In extreme cases, the trauma can lead to complications.

Trauma and swelling of the cardiac pacemaker incision site can be substantially reduced and pain alleviated, if in the hours immediately after implantation, a cold compress is applied and maintained on the site. Conventional cold compresses are often used for this purpose and are effective.

However, to obtain the benefit of the cold compress, the compress must be maintained on the site for several hours, typically up to four hours, which is also typically the time of effective cooling of presently available compresses. Also just as typical, the patient desires to be or is mobile and participates in normal ambulatory activity. While it is always possible to tape the compress to the patient's chest, the removal of the tape may be painful and in almost all cases, causes some irritation and in some patients, severe allergic reaction.

A typical cold compress as is currently available, is sold by Health Corps of Cambridge, Mass. under the brand name Omni Pack. The Omni Pack is simply a strip of woven stretch material with Velcro in fasteners on which a terry cloth pouch has been stitched in the center. The terry cloth pouch provides a rectangular space to hold cold or hot packs while the linear strap of the Omni Pack is wrapped around an arm or leg. The Omni Pack is particularly difficult to apply to a patient and to a cardiac implanation site, which is typically on the front chest wall a few inches above the pectoral muscle. The bandage-type attachment on the Omni Pack, even if extended to encircle the chest, simply slips from position.

Other devices used to hold cold packs includes those such as shown by Meistrell, "Adjustable Wrappable, Stretchable Wrap Sheet," U.S. Pat. No. 4,805,620 (1989), which is a wrapping to hold multiple hot or cold packs adjacent to the chest and arm of the body. Meistrell's device substantially covers the entire neck and shoulder area on one side and wraps across the chest with two chest straps as well as anchoring on the upper arm adjacent the covered shoulder. While this device would be effective for holding a compress in the general area of the implant, it is a severely encumbering device, restricting the comfort and motion of the patient.

Lebold, "Hot and Cold Pack," U.S. Pat. No. 3,889,684 (1975) is more typical of the prior art cold packs. It is comprised simply of a terry cloth pouch into which a cold pack is inserted. The terry cloth pouch has a plurality of Velcro straps and fasteners on its periphery which allow it to be strapped around the user's ankle, neck or limbs. The device, however, is particularly ill adapted for fitting to a large irregular body section, the upper chest-shoulder region, which is required for pacer implant treatment.

Bonner, Jr., "Cold Compress," U.S. Pat. No. 4,556,055 (1985) is another typical prior art example of a device for practicing cryotherapy. Bonner, like Lebold, includes a pocket for insertion of the cold pack and a longitudinal panel connected by Velcro fasteners for wrapping the cold pack around a cylindrically shaped body section or limb. Draping the cold pack in the form of Bonner, like a bandolier, across the shoulder and chest of a patient having a pacemaker implant, is neither comfortable, practical nor effective to securely retain the cold pack over the incision site.

What is needed then is some type of device wherein cryotherapy can be practically and comfortably practiced in connection with cardiac pacemaker implants.

BRIEF SUMMARY OF THE INVENTION

The invention is an apparatus for therapeutic cryotherapy as applied to cardiac pacemaker implantation using a cold compress on a patient comprising a chest pad. An elastic chest strap is arranged and configured for connection to the chest pad. An elastic shoulder strap is arranged and configured for connection to the chest strap and to the chest pad. The chest pad holds the cold compress in proximity to a cardiac pacemaker implantation site on the patient. As a result, trauma resulting from cardiac pacemaker implantation is substantially reduced while mobility and comfort of the patient is substantially enhanced.

The shoulder strap is slidingly coupled to the chest strap. The chest strap has a longitudinal length. The shoulder strap is capable of being arbitrarily positioned along the longitudinal length of the chest strap. The shoulder strap is slidingly coupled to the chest strap by a closed sewn loop defined within the shoulder strap. The chest strap is disposed through the closed loop of the shoulder strap.

The chest strap has two ends. One of the ends is fixed to the chest pad at one side of the chest pad and an opposing one of the two ends is temporarily coupled to at least an opposing side of the chest pad. The chest pad is comprised of an upper lobe and a lower lobe. The chest strap is coupled to the chest pad on the lower lobe of the chest pad. The shoulder strap has two ends. One end is slidingly coupled to the chest strap and an opposing one of the two ends is capable of being temporarily coupled to the chest pad. The shoulder strap is temporarily coupled to the chest pad on the upper lobe of the chest pad.

The cardiac pacemaker implantation is made at an incision site and the chest pad is placed over the incision site. The cold pack is disposed between the chest pad and the incision site. The chest strap is wrapped under tension around the upper torso of the patient and is coupled at both of its ends to the chest pad. The chest strap is placed underneath the arms of the patient. The shoulder strap is adjusted under tension over a selected one of the shoulders of the patient, is slidingly coupled at one end to the chest strap, and is coupled at an opposing end of the shoulder strap to the chest pad to maintain the chest pad over the cardiac pacemaker implantation site notwithstanding normal patient activity, to retain the cold compress in position, and to increase compressive force on the cold compress.

The invention can alternatively be described as an apparatus for providing thermal therapy to cardiac pacemaker incision site on the upper torso of a patient comprising a cold compress component for maintaining a cold compress in firm contact over the cardiac pacemaker implantation site, and a stabilizing component for retaining the cold compress in position over the cardiac pacemaker implantation site regardless of normal patient activity. As a result, thermal therapy is provided to the patient following cardiac pacemaker implantation without substantial restriction on normal activity of the patient.

The cold compress component comprises a first element for contacting a cold compress and a second element for applying a downward compressive force on the first element to maintain the cold compress in intimate contact with the cardiac pacemaker incision site.

The stabilizing component comprises an element for preventing the cold compress element from sliding from the cardiac pacemaker incision site.

The stabilizing component is arranged and configured to retain the cold compress element in position regardless of whether the cold compress element is positioned on left or right side of the patient.

The invention is also characterized as a method of applying a cold compress to a cardiac pacemaker incision site comprising the steps of disposing a cold pack on the incision site and placing a chest pad over the cold pack. An elastic chest strap is wrapped under tension around the upper torso of the patient and under the arms of the patient. The chest strap is connected at its ends to the chest pad to apply a compressive force through the chest pad on the cold pack to maintain the cold pack in contact with the cardiac pacemaker incision site. A shoulder strap is wrapped under tension over the shoulder of the patient. The shoulder strap is attached at opposing ends to the chest strap and to the chest pad to retain the chest pad and cold pack in position over the cardiac pacemaker implantation incision site.

The step of wrapping the shoulder strap under tension over the shoulder of the patient comprises the step of adjusting the shoulder strap under tension at the end coupled to the chest strap so that the length of the shoulder strap between the chest strap and the chest pad is minimized.

The step of wrapping the chest strap under tension around the torso of the patient comprises the step of temporarily coupling one end of the chest strap to the chest pad. The ends of the chest strap are coupled to the chest pad on a lower lobe of the chest pad.

The step of wrapping the shoulder strap under tension over the shoulder of the patient comprises the step of temporarily coupling one end of the shoulder strap to the chest pad. The opposing end of the shoulder strap is slidingly coupled to the chest strap and is disposed under tension around the back of the patient.

The step of wrapping the shoulder strap over the shoulder of the patient comprises the step of temporarily coupling one end of the shoulder strap to the chest pad. The opposing end of the shoulder strap is slidingly coupled to the chest strap and disposed under tension around the back of the patient.

The invention may be better visualized by turning to the following drawings.

The invention and its various embodiments may now be better understood by turning to the following detailed description.

DETAILED DESCRIPTION OF THE PREFERRED EMBODIMENTS

The invention is a harness for holding a cold pack on the upper torso of a patient who has received a cardiac pacemaker implant. The implants are normally subcutaneously disposed in the upper chest portion of the patient. A therapeutic device for providing cold treatments to cardiac pacemaker implantation patients is comprised of a bilobed chest pad having an elastic chest strap connected thereto. The chest strap is fixed at one end to the lower lobe of the chest pad and is wrapped around the torso of the patient under tension and temporarily is coupled to the opposing portion of the lower lobe of the chest pad. The cold compress, which is placed behind the chest pad over the incision site, is thereby firmly kept in contact with the incision site. A shoulder strap is slidingly coupled at one end to the chest strap and is positioned on the back of the patient and wrapped under tension behind the back and over the shoulder of the patient, which shoulder is adjacent to the incision site. The end of the shoulder strap is then temporarily coupled to the upper lobe of the chest pad. The shoulder strap, substantially adds to the compression on the cold compact and retains the chest pad and shoulder strap in place notwithstanding normal activity of the patient. As a result, the patient is able to move about and engage in normal activities very soon after cardiac implantation and yet continue to receive the benefits of thermal therapy to minimize the trauma normally associated with a subcutaneous cardiac pacemaker implantation.

Figure 1:
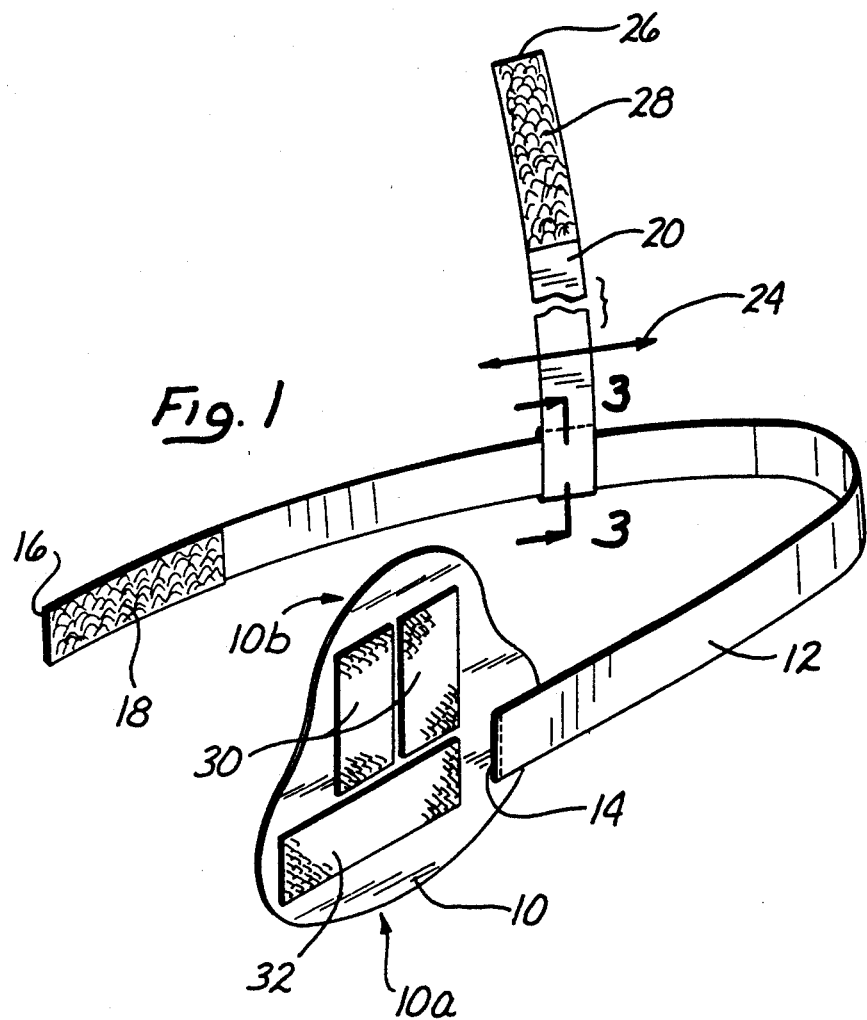
FIG. 1 is a perspective view of the invention shown in a detached configuration.
Figure 3:
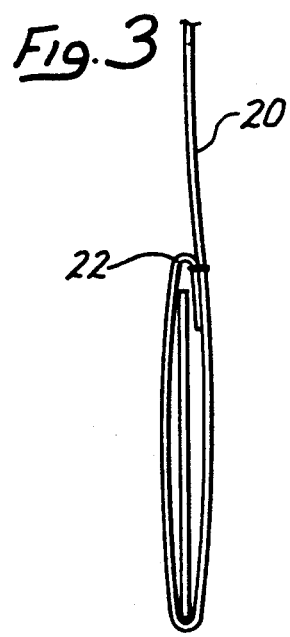
FIG. 3 is a cross-sectional view of the attachment of the shoulder strap to the chest strap of the invention as seen through section lines 3—3 of FIG. 1.

Turning first to FIG. 1, which depicts a perspective view of the invention shown in a detached configuration, the illustrated embodiment is shown as being comprised of a chest pad 10 under which a cold compress (not shown) is placed. Chest pad 10 holds the cold compress on the incision site on the patient's chest. Chest pad 10 may also include a stitched rear pocket (not shown) for holding the compress, although after final adjustment, the temporary holding function of such a pocket may become superfluous. In the illustrated embodiment chest pad 10 has two lobes, a lower enlarged portion or lobe 10a adapted to provide a broad surface for applying a compressive force to the compress, and an upper smaller portion or lobe 10b adapted for connection to an elastic shoulder strap 20 for positioning and retention of position. An elastic chest strap 12 has one end 14 sewn to chest pad 10. Opposing end 16 of chest strap 12 has a Velcro fastener 18. Slidingly coupled to chest strap 12 is a shoulder strap 20. Shoulder strap 20 is slidingly coupled to chest strap 12 by means of a sewn loop 22 best depicted in cross-section in FIG. 3. Sewn loop 22 encircles chest strap 12 and permits chest strap 12 to be adjusted at any point along the longitudinal length of chest strap 12. Loop 22 is sewn to itself so that chest strap 20 may be translated in either direction along chest strap 12 as diagrammatically depicted by arrow 24 in FIG. 1. Opposing end 26 of chest strap 20 has a Velcro fastener 28 stitched or adhered thereto.

Figure 2:
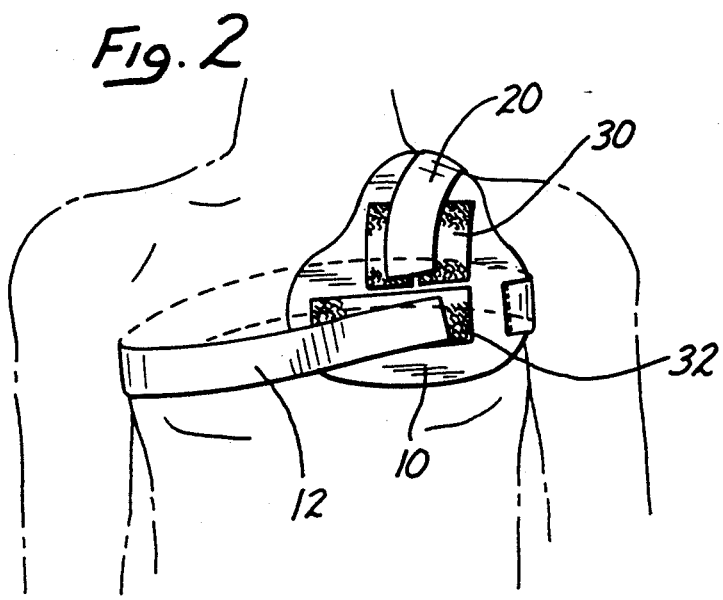
FIG. 2 is a front elevational view of the invention shown as applied to a patient.

The opposing side of chest pad 10 has a plurality of complementary Velcro fastening sections 30 sewn or attached to the outside of chest pad 10, as best depicted in FIG. 1. The portion of chest strap 12 nearest end 16 of chest pad 10 is placed beneath the adjacent arm of the patient, stretched behind his back and thence under the opposite arm and stretched across the chest as shown in FIG. 2 and attaches to a Velcro fastening pad 32. Similarly, fastener 28 of shoulder strap 20 is placed and stretched over either the left or right shoulder of the patient and similarly attached to one of Velcro fasteners 34. In the illustrated embodiment, fastening pads 30 and 32 are hook fasteners, while fastening pads 18 and 28, are the eye or felt portions of the Velcro connectors.

Therefore, the pad through the adjustability of shoulder strap 20, both in terms of the length of its attachment as well as its position along chest strap 12, allows chest pad 10 to be snugly placed over the appropriate incision site on the patient regardless of a wide variety of patient sizes and shapes. The elasticity of stretched chest strap 12 provide enough compressive force to insure good thermal contact between the cold compress placed behind the rear surface of chest pad 10 and the incision site. The elasticity of stretched shoulder strap 20 keeps the cold compress, which is by far the most massive element in the assembly, pulled up over the incision site, which is usually high on the upper chest and substantially increases the compressive force on the cold compress. In addition, shoulder strap 20 pulls upper lobe 10b of chest pad 10 in against the chest thereby tending to make an enclosure over the cold compress. This enclosure also creates a downward force on the cold compress which tends to neutralize the upward force on the cold compress created by the compression of chest strap 12 against lower lobe 10a, which latter compressive force might otherwise tend to squeeze the compress up and out from underneath chest pad 10.

Chest strap 12 can be snugly wrapped around the patient's chest underneath the patient's arms and can provide enough compression to keep the cold compress against the incision site even though chest plate 10 need not have any retaining pocket in to which the cold compress is placed or any other means for fixing the cold compress to the rear surface of chest plate 10. The retention of the cold compress is facilitated by both the snugness of the fit which can be adjusted by chest strap 12 along with the connection of the ends of chest strap 12 to a lower half or lobe of chest plate 10. However, in order to prevent chest plate 10 from sliding down during movement and to further ensure the secure retention and pressure of the cold compress against the incision site, shoulder strap 20 is adjusted so that it is disposed comfortably and snugly over the patient's shoulder and connected to Velcro fasteners 30 on top half portion of chest pad 10. Therefore, normal movement and flexing of the patient is generally insufficient to cause chest strap 12 and chest pad 10 from working down over the generally inwardly tapering torso of the patient.

It is expressly understood that many other embodiments and modifications are contemplated as included within the device although not specifically illustrated. For example, it is expressly contemplated that Velcro fasteners may be placed in different positions or switched, namely a felt fastener exchange for hook fastener and visa versa. Similarly, although Velcro is preferred attachment means, any other attachment means, including low bonded pressure adhesives, now known or later devised, may also be equivalently substituted. Still further, although it is expressly contemplated that no pocket, strap, tape or other means is necessary to secure the cold compress to chest pad 10, the inclusion of such elements in the invention are to be included and are contemplated. Complementary Velcro fasteners can also be provided on the outside ends of chest strap 12 so that chest strap 12 can be stretched and overlapped at its opposing ends on chest pad 10 and thus connected together.

We claim:

1. An apparatus for therapeutic cryotherapy as applied to cardiac pacemaker implantation adapted for use with a cold compress on a patient comprising:
   a chest pad;
   a single, circumferential elastic chest strap arranged and configured for connection to said chest pad and encircling the chest of said patient;
   a separate and adjustable elastic shoulder strap arranged and configured for connection to said chest strap and to said chest pad without any restricting contact of said shoulder strap with any portion of the arm of said patient, said elastic shoulder strap adapted to be positioned only over the shoulder of said patient and not across any portion of the arm of said patient, said chest pad adapted for holding said cold compress in proximity to a cardiac pacemaker implantation site on said patient, wherein said shoulder strap has two ends, one end being slidingly coupled to said chest strap and an opposing one of said two ends being capable of being temporarily coupled to said chest pad,
   whereby trauma resulting from cardiac pacemaker implantation is substantially reduced while mobility and comfort of said patient is substantially enhanced.

2. The apparatus of claim 1 wherein said chest strap has a longitudinal length, said shoulder strap capable of being arbitrarily positioned along said longitudinal length of said chest strap.

3. The apparatus of claim 2 wherein said shoulder strap is slidingly coupled to said chest strap by a closed sewn loop defined within said shoulder strap, said chest strap being disposed through said closed loop of said shoulder strap.

4. The apparatus of claim 1 wherein said chest pad is comprised of an upper lobe and a lower lobe, and said shoulder strap is temporarily coupled to said chest pad on said upper lobe of said chest pad.

5. An apparatus for therapeutic cryotherapy as applied to cardiac pacemaker implantation for use with a cold compress on a patient comprising:
   a chest pad;
   an elastic chest strap arranged and configured for connection to said chest pad;
   an elastic shoulder strap arranged and configured for connection to said chest strap and to said chest pad, said chest pad for holding said cold compress in proximity to a cardiac pacemaker implantation site on said patient, wherein said shoulder strap has two ends, one end being slidingly coupled to said chest strap and an opposing one of said two ends being capable of being temporarily coupled to said chest pad, whereby trauma resulting from cardiac pacemaker implantation is substantially reduced while mobility and comfort of said patient is substantially enhanced.

* * * * *